(12) United States Patent
Xu et al.

(10) Patent No.: US 8,709,182 B2
(45) Date of Patent: Apr. 29, 2014

(54) THERMAL PRESSURE WELDING APPARATUS AND THERMAL PRESSURE WELDING METHOD FOR WAISTS OF INCONTINENT PANTS AND TRAINING PANTS

(75) Inventors: Yuanquan Xu, Zhejiang (CN); Guodong Wang, Zhejiang (CN); Shijin Li, Zhejiang (CN); Wei Xu, Zhejiang (CN)

(73) Assignee: Hangzhou Creator Machinery Manufacture Co., Ltd., Hangzhou (CN)

( * ) Notice: Subject to any disclaimer, the term of this patent is extended or adjusted under 35 U.S.C. 154(b) by 352 days.

(21) Appl. No.: 12/993,078
(22) PCT Filed: May 11, 2010
(86) PCT No.: PCT/CN2010/072598
§ 371 (c)(1), (2), (4) Date: Sep. 6, 2011
(87) PCT Pub. No.: WO2010/142180
PCT Pub. Date: Dec. 16, 2010

(65) Prior Publication Data
US 2011/0303360 A1    Dec. 15, 2011

(30) Foreign Application Priority Data
Jun. 12, 2009    (CN) .......................... 2009 1 0099801

(51) Int. Cl.
*B32B 37/00* (2006.01)
(52) U.S. Cl.
USPC ........... 156/64; 156/228; 156/359; 156/583.5
(58) Field of Classification Search
USPC ........... 156/64, 228, 359, 361, 366, 555, 580, 156/582, 583.1, 583.5
See application file for complete search history.

(56) References Cited

U.S. PATENT DOCUMENTS

| | | | |
|---|---|---|---|
| 2,572,251 A | | 11/1951 | Arnold |
| 4,921,569 A | * | 5/1990 | Held ........................ 156/380.6 |
| 5,910,230 A | * | 6/1999 | Seki et al. ................... 156/470 |
| 6,227,271 B1 | * | 5/2001 | Pourmand et al. ............ 156/498 |
| 6,435,247 B1 | * | 8/2002 | Kerr .............................. 156/555 |

FOREIGN PATENT DOCUMENTS

| | | |
|---|---|---|
| CN | 1807081 A | 7/2006 |
| CN | 101347879 A | 1/2009 |
| CN | 101590693 A | 12/2009 |

OTHER PUBLICATIONS

International Search Report mailed Aug. 19, 2010, in corresponding International Application No. PCT/CN2010/072598, filed May 11, 2010, 5 pages.
International Search Report mailed Aug. 19, 2010, in corresponding International Application No. PCT/CN2010/072598, filed May 11, 2010, 12 pages.

* cited by examiner

*Primary Examiner* — James Sells
(74) *Attorney, Agent, or Firm* — Christensen O'Connor Johnson Kindness PLLC

(57) ABSTRACT

The present invention relates to a thermal pressure welding apparatus for the waist of incontinent pants and training pants and a thermal pressure welding method. The apparatus can thermal pressure weld the waist of incontinent pants and training pants consists of multiple layers of non-woven fabric in a fast, accurate and secure manner. An upper synchronous transmission mechanism and a lower synchronous transmission mechanism are disposed vertically opposed, by means of a shaft, on a side of a vertical frame. The upper synchronous transmission surface of the upper synchronous transmission mechanism and the synchronous transmission surface of the lower synchronous transmission mechanism are opposed. A plurality of toothed pressing blocks are spacedly opposed on the upper synchronous transmission surface and the lower synchronous transmission surface respectively. An electrothermal tube inside the toothed pressing block is connected to supply lines in a conductive ring through extendable wires and wiring flanges, which conductive ring is rotated synchronously with the upper synchronous transmission mechanism and the lower synchronous transmission mechanism. The plane rails moving up and down are positioned on the inner sides of the synchronous transmission surfaces of the upper synchronous transmission mechanism and the lower synchronous transmission mechanism respectively and the rail surfaces of the plane rails are vertically opposed.

9 Claims, 2 Drawing Sheets

THERMAL PRESSURE WELDING APPARATUS AND THERMAL PRESSURE WELDING METHOD FOR WAISTS OF INCONTINENT PANTS AND TRAINING PANTS

TECHNICAL FIELD

The present invention is directed to a thermal pressure welding apparatus and a thermal pressure welding method for quickly, accurately and reliably thermal pressure welding waists of incontinent pants and training pants, which waists are constituted by multiple layers of non-woven fabric. The present invention belongs to the field of manufacture of a non-woven fabric thermal pressure welding apparatus.

DESCRIPTION OF THE RELATED ART

The applicant owns the patent No. CN1234308C, titled "a forming compound device and a forming method for infant and child training pants", wherein a patterned die wheel or roller cooperates with an ultrasonic die head in a welding mechanism. When the material for waist and leg of the infant and child training pants are passing through the gap between the patterned die wheel or roller and the ultrasonic die head, the ultrasonic waves emitted from the ultrasonic die head cause the molecules between the material of the convex portion of the patterned die wheel and the material contacting surface to vibrate to generate heat energy, thereby the two layers of material is rolled and combined by the convex portion of the patterned die wheel so that the waist pieces on both sides of the infant and child training pants are welded. Two following plates in a following mechanism follow coaxially with the patterned die wheel and drive the ultrasonic die head moving forward and backward. The gap between the ultrasonic die head and the die wheel is kept constant. The aspects to be improved lie in that: Firstly, due to the small diameter of the shaft fitted-over by the patterned die wheel, the wheel surface of the patterned die wheel cooperates, by a narrow surface rather than a wide surface, with the end surface of the welding head of an ultrasonic welding generator. Thus it is suitable only for a gradually welding of welded pieces (FIG. 3) not for a onetime instant welding thereof, and the welding reliability is not satisfactory. Secondly, since there is only one group of ultrasonic welding heads on the surface of the patterned die wheel corresponding thereto, only onetime welding can be realized. It is impossible to implement a second, third, or multiple times welding. In particular, it is impossible to effectively weld multiple layers of welded pieces. Thirdly, The welding efficiency directly affects the production efficiency of the production apparatus for incontinent pants, infant training pants, infant releasing pants, sanitary napkins and other sanitary products. Fourthly, since the patterned die wheel does not have a preheating structure, the welding speed is slow and welding strength is weak to the welded pieces between the wheel surface of the patterned die wheel and the welding head of the ultrasonic welding generator. Fifthly, For the same material, the same thickness, the same welding speed, the same power, the same frequency, the same amplitude, the same ultrasonic welding mould, the same mould shape (for the patterned die wheel or the patterned block), the same patterned toothed mould and the same welding gap, since the prior art presents a narrow surface-welding for the welded pieces, a short welding time and a welding mould lacking a preheating device, the welding speed is slow and the welding strength is weak. Moreover, it is impossible to weld thick or multiple layers of the welded pieces.

SUMMARY OF THE INVENTION

The object of the present invention is to overcome the disadvantages in the prior art. The present invention is direct to a thermal pressure welding apparatus for the waist of incontinent pants and training pants and a thermal pressure welding method, the apparatus being capable of thermal pressure welding the waist of incontinent pants and training pants consists of more than six layers of non-woven fabric with glue and elastic in a fast, accurate and secure manner.

The technical solution is to fuse multiple layers of PE or PP type material together by heating and pressing for high-speed production of incontinent pants and training pants, wherein the temperature, the pressure and the pressing time are crucial factors to realize the present application. In particular:

1. The first technical feature of the invention lies in that an upper synchronous transmission mechanism and a lower synchronous transmission mechanism are disposed vertically opposed and the upper synchronous transmission surface of the upper synchronous transmission mechanism and the synchronous transmission surface of the lower synchronous transmission mechanism are opposed. The object firstly lies in that the transmission surfaces of the upper and lower synchronous transmission mechanisms rotate synchronously with respect to each other, and the incontinent pants or training pants held between them rotate synchronously with the upper, lower synchronous transmission surfaces. Secondly, the reliability of high-speed welding for the incontinent pants and training pants depends on the time for pressure welding the waists of the incontinent pants and training pants, which in turn is determined by the length of a rail, which length is adjusted properly according to the production speed. The length of a rail can be properly increased when the production speed is high and can be properly reduced when the production speed is low. The length of a rail depends on the production speed per minute of the incontinent pants and training pants.

2. The second technical feature of the invention lies in that a plurality of toothed pressing blocks are spacedly opposed on the upper synchronous transmission surface and the lower synchronous transmission surface respectively. Since electrothermal tubes inside the toothed pressing blocks not only heat the toothed pressing blocks, but also is connected to supply lines in a conductive ring through extendable wires and wiring flanges, which conductive ring is rotated synchronously with the upper synchronous transmission mechanism and the lower synchronous transmission mechanism, the supply lines inside the conductive rings will not be interwound when rotating at a high speed synchronously with the upper synchronous transmission mechanism and the lower synchronous transmission mechanism.

3. The third technical feature of the invention lies in that the plane rails moving up and down are positioned on the inner sides of the synchronous transmission surfaces of the upper synchronous transmission mechanism and the lower synchronous transmission mechanism respectively and the rail surfaces of the plane rails are vertically opposed. Since one of the essential factors for quickly welding the waists of the incontinent pants and training pants is pressure, the reliable welding of multiple layers of non-woven fabric, particularly those with glue and elastic, can be achieved only when the pressure required for welding multiple layers of non-woven fabric is reached. Thus, said plane rails moving up and down are provided with upper and lower plane rails and upper and lower pneumatic cylinder at inner sides thereof respectively. The upper and lower pneumatic cylinder drives the upper and lower plane rails to move up and down according to the instructions of the control panel so as to realize the pressure welding of the waists of the incontinent pants and training pants.

4. The fourth technical feature of the invention lies in that rollers are provided on the back surface of the toothed pressing block. Thus, not only the synchronous rotation of the toothed pressing blocks with of the upper and lower synchronous transmission surfaces in the upper and lower synchronous transmission mechanisms is obtained, and but also the plane rails moving up and down applying pressure to the toothed pressing blocks by rolling mating with the rollers can be realized.

The technical solution 1 is: a thermal pressure welding apparatus for waists of incontinent pants and training pants, wherein an upper synchronous transmission mechanism and a lower synchronous transmission mechanism are disposed vertically opposed, by means of a shaft, on a side of a vertical frame; the upper synchronous transmission surface of the upper synchronous transmission mechanism and the synchronous transmission surface of the lower synchronous transmission mechanism are opposed; a plurality of toothed pressing blocks are spacedly opposed on the upper synchronous transmission surface and the lower synchronous transmission surface respectively; an electrothermal tube inside the toothed pressing block is connected to supply lines in a conductive ring through extendable wires and wiring flanges, which conductive ring is rotated synchronously with the upper synchronous transmission mechanism and the lower synchronous transmission mechanism; the plane rails moving up and down are positioned on the inner sides of the synchronous transmission surfaces of the upper synchronous transmission mechanism and the lower synchronous transmission mechanism respectively and the rail surfaces of the plane rails are vertically opposed.

The technical solution 2: a thermal pressure welding method by a thermal pressure welding apparatus for waists of incontinent pants and training pants, wherein the apparatus includes a control panel; the control panel instructs waists of incontinent pants and training pants of PE or PP type, which waists have multiple layers and need to be welded, to be delivered to among the toothed pressing blocks between the upper synchronous transmission surface and the lower synchronous transmission surface of the upper synchronous transmission mechanism and the lower synchronous transmission mechanism; while the upper and lower pneumatic cylinders apply pressure to the toothed pressing blocks positioned between the upper synchronous transmission surface and the lower synchronous transmission surface by the upper and lower plane rails, the waists of incontinent pants and training pants among the toothed pressing blocks are welded and at same time are rotated synchronously with the upper synchronous transmission surface and the lower synchronous transmission surface; after pressure welding the waists for a preset time, the control panel instructs the upper and lower pneumatic cylinders to reset and drives the upper and lower plane rails to be retracted; the incontinent pants and training pants with waists welded then proceed to a next process.

As comparing with the prior art, the present invention has the a plurality of advantages. Firstly, the present apparatus can replace an expensive ultrasonic welding apparatus, and more importantly, solve the technical problem of quickly and reliably welding multiple layers (more than 5 layers) that an ultrasonic welding apparatus can not realize, thereby quickly and reliably weld up to 120 pieces per minute for the waists of incontinent pants and training pants of up to eight layers of non-woven fabric, and dramatically reduce the manufacture and maintenance cost. Secondly, the temperature of each toothed pressing block can be controlled individually, thereby the temperature of each working unit is more accurate and real and the welding reliability is higher. Thirdly, since long plane rails are used, the pressing time is greatly extended and the thermal welding effects are improved. As comparing with the pressing manner by cylinder rolls in the prior art, the operation speed of the apparatus is eventually greatly increased. Fourthly, the structure is simple, the operation is convenient, and the operators can control and maintain the apparatus easily. Fifthly, the structure design is novel, independent, and reliable, and the production efficiency is high.

BRIEF DESCRIPTION OF THE ACCOMPANYING DRAWINGS

DETAILED DESCRIPTION OF THE PREFERRED EMBODIMENTS

Embodiment 1

Figure 1:
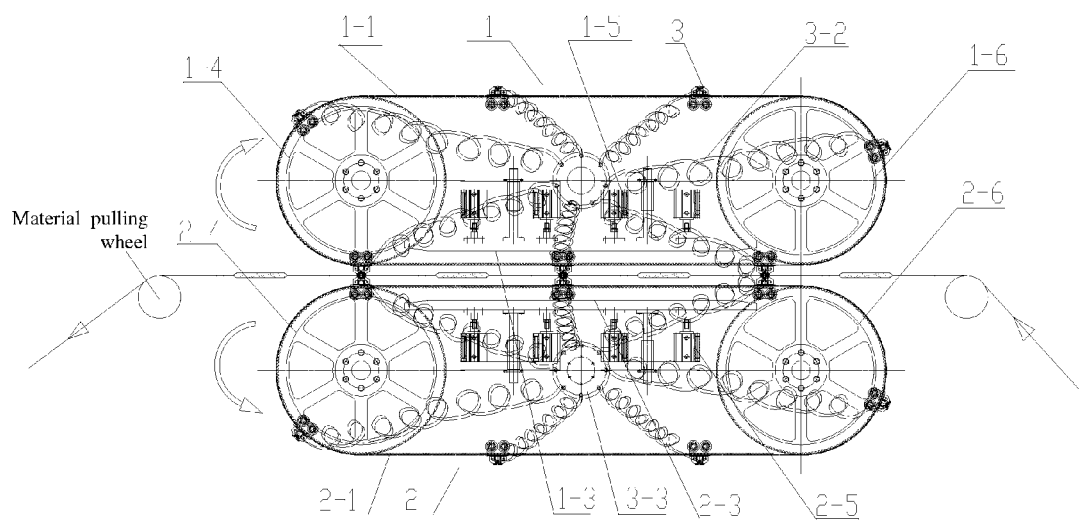
FIG. 1 is a schematic configuration diagram of a thermal pressure welding apparatus for waists of incontinent pants and training pants.
Figure 2:
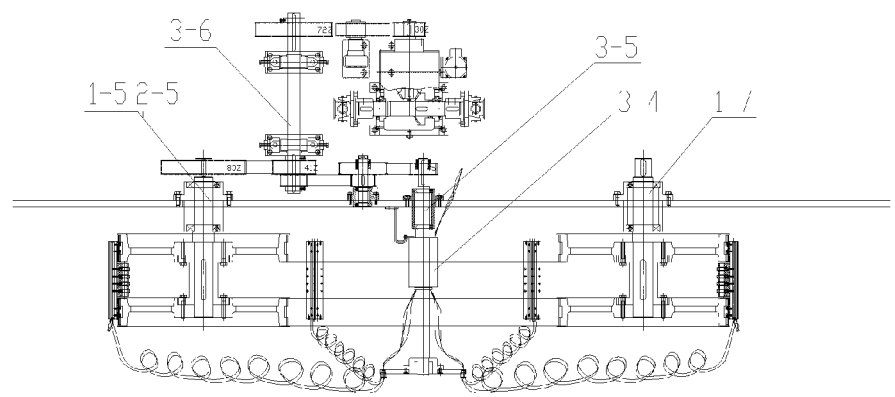
FIG. 2 is a schematic configuration diagram of a synchronous electric device matched with an upper and lower synchronous transmission mechanisms.
Figure 3:
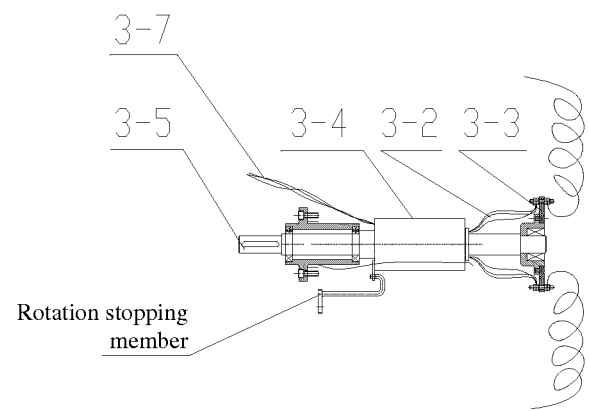
FIG. 3 is a schematic configuration diagram of an electric conductive assembly.

FIGS. 1-3 show a thermal pressure welding apparatus for waists of incontinent pants and training pants. An upper synchronous transmission mechanism 1 and a lower synchronous transmission mechanism 2 are disposed vertically opposed, by means of a shaft, on a side of a vertical frame 4. The upper synchronous transmission surface 1-1 of the upper synchronous transmission mechanism 1 and the synchronous transmission surface 2-1 of the lower synchronous transmission mechanism 2 are opposed. A plurality of toothed pressing blocks 3 are spacedly opposed on the upper synchronous transmission surface 1-1 and the lower synchronous transmission surface 2-1 respectively. Said upper synchronous transmission surface 1-1 and lower synchronous transmission surface 2-1 belong to a synchronous belt transmission or a synchronous chain transmission. Rollers 3-8 are provide on the back surface of the toothed pressing block 3 and are mated with the plane rails 1-3 or 2-3 in a pressure rolling manner. An electrothermal tube 3-1 inside the toothed pressing block 3 is connected to supply lines in a conductive ring 3-4 through extendable wires 3-2 and wiring flanges 3-3, which conductive ring 3-4 is rotated synchronously with the upper synchronous transmission mechanism 1 and the lower synchronous transmission mechanism 2. The plane rails 1-3 and 2-3 moving up and down are positioned on the inner sides of the synchronous transmission surfaces of the upper synchronous transmission mechanism 1 and the lower synchronous transmission mechanism 2 respectively and the rail surfaces of the plane rails 1-3 and 2-3 are vertically opposed. Said wiring flange 3-3 is connected to the conductive ring 3-4 and drives the extendable wires thereon to rotate synchronously with the upper and lower synchronous transmission mechanisms 1 and 2. Input supply lines 3-7 are stationary. The outer ring of the conductive ring 3-4 is stationary and the inner ring thereof rotates synchronously with a central shaft 3-5. The conductive ring 3-4 is connected to the central shaft 3-5 and the central shaft 3-5 is rotated synchronously with driving wheels 1-4 or 2-4 by gear engagements. Said upper synchronous transmission mechanism 1 or lower synchronous transmission mechanism 2 includes a driving wheel 1-4 or 2-4, a driving shaft 1-5 or 2-5, a driven wheel 1-6 or 2-6, a driven shaft 1-7 or 2-7 and the synchronous transmission surface 1-1 or 2-1 of the transmission belt. The driving wheel 1-4 or 2-4 is driven by the driving shaft 1-5 or 2-5 which is rotated by transmission mechanisms 3-6. The driven wheel 1-6 or 2-6 is connected to the driven shaft 1-7 or 2-7. The synchronous transmission surface 1-1 or 2-1 is positioned on the driving wheel 1-4 or 2-4 and the driven wheel 1-6 or 2-6 of the upper or lower synchronous transmission mechanism 1 or 2 respectively. Said plane rail 1-3 or 2-3 moving up and down includes upper and lower plane rails and upper and lower pneumatic cylinder 1-5 and 2-5 respectively. The upper and lower pneumatic cylinder 1-5 and 2-5 are positioned on the inner sides of the upper and lower plane rails and drives the upper and lower plane rails to move up and down.

Particularly, the driving wheel 1-4 or 2-4 is rotated by the driving shaft 1-5 or 2-5, and the driving wheel 1-4 or 2-4 and the driven wheel 1-6 or 2-6 support the synchronous belts or chains 1-1 or 2-1 and drive them to rotate. The synchronous belt or chain 1-1 or 2-1 is used to connect the toothed pressing blocks 3 to distribute them in predetermined positions and drive them. The toothed pressing blocks 3 press the material to form corresponding patterns thereon. The electrothermal tube 3-1 supplies heat required for welding. The plane rail 1-3 or 2-3 support the toothed pressing blocks 3 and transmits pressure thereto during the linear movement. The central shaft 3-5 and the conductive ring 3-4 support the extendable wires 3-2, and continuously supply electric power to the moving part, i.e. the electrothermal tube 3-1. The pneumatic cylinders 1-5 and 2-5 provide pressure required for thermal welding. The transmission devices (mechanisms) 3-6 transmit power to operate the whole equipment in a predetermined speed. Under a certain transmission ratio, the central shaft 3-5 and the driving wheel are moved in a predetermined speed with synchronized phases.

The synchronous belts or chains 1-1 and 2-1 of a preselected specification are mounted between the driving wheel 1-4 or 2-4 and the driven wheel 1-6 or 2-6. Then several toothed pressing blocks 3 are mounted to the synchronous belts or chains 1-1 and 2-1 at preset positions. The electrothermal tubes 3-1 are mounted inside each group of toothed pressing blocks 3 and are coupled with the outgoing lines end of the central shaft 3-5 by the extendable elastic wires 3-2. The central shaft 3-5 and the inner ring of the rotary conductive ring 3-4 as well as the outgoing lines are fixed together to ensure that the central shaft 3-5 and the circumferential phase of the output lines are synchronized with the toothed pressing blocks 3 when the toothed pressing blocks 3 is moved with the synchronous belts or chains 1-1 and 2-1. The moving speed of the central shaft 3-5 can be regulated by an intermediate transmission mechanism to realize a synchronous movement with the toothed pressing blocks 3, thereby ensuring that the extendable wires 3-2 will not be interwound.

Each electrothermal tube 3-1 inside the toothed pressing blocks 3 is powered by separate lines and the temperature is controlled by independent temperature sensors and temperature control instruments. The manufacture technology of an electrothermal tube belongs to prior art and will not be described here. The power of the electrothermal tube 3-1 is sufficient to cause the toothed pressing blocks 3 to reach the required operation temperature in short time and ensures the heat loss to be timely supplemented during the operation.

The upper and lower toothed pressing blocks 3 each moves linearly along respective plane rail 1-3 or 2-3 when entering the operation process. The back surface of each toothed pressing block 3 is provided with rollers 3-8 which roll on the plane rails. At the same time several groups of pneumatic cylinders 1-5 or 2-5 located on the upper and lower plane rail 1-3 or 2-3 apply pressure thereto. The pressure of the pneumatic cylinders 1-5 and 2-5 is adjustable and the stroke thereof can be precisely adjusted. Their pressure is transmitted to the toothed pressing blocks 3 through the rollers 3-8 and finally to the pressed material.

The pressing time depends on the lengths of the plane rails 1-3 and 2-3, which lengths can be properly adjusted according to the manufacture speed.

Embodiment 2

On the base of Embodiment 1, a thermal pressure welding method by the thermal pressure welding apparatus for waists of incontinent pants and training pants is provided. The apparatus includes a control panel instructing waists of incontinent pants and training pants of PE or PP type, which waists have multiple layers and need to be welded, to be delivered to among the toothed pressing blocks 3 between the upper synchronous transmission surface 1-1 and the lower synchronous transmission surface 2-1 of the upper synchronous transmission mechanism 1 and the lower synchronous transmission mechanism 2. Toothed pressing blocks 3 are provided with the rollers 3-8 on the back surfaces thereof and are mated with the plane rail 1-3 or 2-3 in a pressure rolling manner. While the upper and lower pneumatic cylinders 1-5 and 2-5 apply pressure to the toothed pressing blocks 3 positioned between the upper synchronous transmission surface 1-1 and the lower synchronous transmission surface 2-1 by the upper and lower plane rails, the waists of incontinent pants and training pants are welded and at same time are rotated synchronously with the upper synchronous transmission surface 1-1 and the lower synchronous transmission surface 2-1 under the action of the toothed pressing blocks 3. At the same time, the rollers 3-8 located on the back surfaces of the toothed pressing blocks 3 are mated with the plane rail 1-3 or 2-3 in a pressure rolling manner, the force applied by the plane rail 1-3 or 2-3 is transmitted to the toothed pressing blocks 3 directly through the rollers 3-8, and the toothed surfaces of the toothed pressing blocks 3 directly act on the multiple layers of material being welded. After pressure welding a preset time, the control panel instructs the upper and lower pneumatic cylinders 1-5 and 2-5 to reset and drives the upper and lower plane rails to be retracted. The incontinent pants and training pants with waists welded then proceed to a next process. Electrothermal tubes 3-1 are provided inside the toothed pressing blocks 3 and heat the toothed pressing blocks 3 to a required temperature under the instructions of the control panel.

It should be understood that although the invention is described in detail by means of the embodiments mentioned above, the description is only intended to illustrate the idea of the invention but not to limit it. Any addition, omission or combination, which does not go beyond the idea of the invention, is fallen into the scope claimed by the invention.

What claimed is:

1. A thermal pressure welding apparatus for waists of incontinent pants and training pants, characterized in that: an upper synchronous transmission mechanism and a lower synchronous transmission mechanism are disposed vertically opposed, by means of a shaft, on a side of a vertical frame; the upper synchronous transmission surface of the upper synchronous transmission mechanism and the synchronous transmission surface of the lower synchronous transmission mechanism are opposed; a plurality of toothed pressing blocks are spacedly opposed on the upper synchronous transmission surface and the lower synchronous transmission surface respectively; an electrothermal tube inside the toothed pressing block is connected to supply lines in a conductive ring through extendable wires and wiring flanges, which conductive ring is rotated synchronously with the upper synchronous transmission mechanism and the lower synchronous transmission mechanism; plane rails moving up and down are positioned on the inner sides of the synchronous transmission surfaces of the upper synchronous transmission mechanism and the lower synchronous transmission mechanism respectively and the rail surfaces of the plane rails are vertically opposed.

2. The thermal pressure welding apparatus for waists of incontinent pants and training pants claimed according to claim 1, characterized in that: said wiring flange is connected to the conductive ring and drives the extendable wires thereon to rotate synchronously with the upper and lower synchronous transmission mechanisms.

3. The thermal pressure welding apparatus for waists of incontinent pants and training pants claimed according to claim 1, characterized in that: said upper synchronous transmission surface and lower synchronous transmission surface belong to a synchronous belt transmission or a synchronous chain transmission.

4. The thermal pressure welding apparatus for waists of incontinent pants and training pants claimed according to claim 1, characterized in that: the conductive ring is connected to the central shaft and the central shaft is rotated synchronously with driving wheels by gear engagements.

5. The thermal pressure welding apparatus for waists of incontinent pants and training pants claimed according to claim 1, characterized in that: said upper synchronous transmission mechanism or lower synchronous transmission mechanism includes a driving wheel, a driving shaft, a driven wheel, a driven shaft and the synchronous transmission surface of the transmission belt; the driving wheel is driven by the driving shaft which is rotated by transmission mechanisms; the driven wheel is connected to the driven shaft; the synchronous transmission surface is positioned on the driving wheel and the driven wheel of the upper or lower synchronous transmission mechanism respectively.

6. The thermal pressure welding apparatus for waists of incontinent pants and training pants claimed according to claim 1, characterized in that: said plane rail moving up and down includes upper and lower plane rails and upper and lower pneumatic cylinder respectively; the upper and lower pneumatic cylinder are positioned on the inner sides of the upper and lower plane rails and drives the upper and lower plane rails to move up and down.

7. The thermal pressure welding apparatus for waists of incontinent pants and training pants claimed according to claim 1, characterized in that: rollers are provide on the back surface of the toothed pressing block and are mated with the plane rails in a pressure rolling manner.

8. A thermal pressure welding method by a thermal pressure welding apparatus for waists of incontinent pants and training pants, the apparatus includes a control panel; the control panel instructs to deliver waists of incontinent pants and training pants of PE or PP type to among toothed pressing blocks between the upper synchronous transmission surface and the lower synchronous transmission surface of the upper synchronous transmission mechanism and the lower synchronous transmission mechanism, which waists have multiple layers and need to be welded; while the upper and lower pneumatic cylinders apply pressure to the toothed pressing blocks positioned between the upper synchronous transmission surface and the lower synchronous transmission surface by upper and lower plane rails, the waists of incontinent pants and training pants among the toothed pressing blocks are welded and at same time are rotated synchronously with the upper synchronous transmission surface and the lower synchronous transmission surface; after pressure welding the waists for a preset time, the control panel instructs the upper and lower pneumatic cylinders to reset and drives the upper and lower plane rails to be retracted; the incontinent pants and training pants with waists welded then proceed to a next process.

9. The thermal pressure welding method by a thermal pressure welding apparatus for waists of incontinent pants and training pants claimed according to claim 8, characterized in that: electrothermal tubes are provided inside the toothed pressing blocks and heat the toothed pressing blocks to a required temperature under the instructions of the control panel.

* * * * *